(12) United States Patent
Sato (10) Patent No.: US 9,804,381 B2
(45) Date of Patent: Oct. 31, 2017

(54) ENDOSCOPE OBJECTIVE OPTICAL SYSTEM

(71) Applicant: OLYMPUS CORPORATION, Hachioji-shi, Tokyo (JP)

(72) Inventor: Shinya Sato, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/585,579

(22) Filed: May 3, 2017

(65) Prior Publication Data
US 2017/0235122 A1 Aug. 17, 2017

Related U.S. Application Data

(63) Continuation of application No. PCT/JP2016/061828, filed on Apr. 12, 2016.

(30) Foreign Application Priority Data

Apr. 24, 2015 (JP) .................................. 2015-089661

(51) Int. Cl.
*G02B 13/04* (2006.01)
*G02B 23/24* (2006.01)
(Continued)

(52) U.S. Cl.
CPC ........ *G02B 23/243* (2013.01); *A61B 1/00096* (2013.01); *A61B 1/00163* (2013.01); *G02B 9/12* (2013.01); *G02B 13/04* (2013.01)

(58) Field of Classification Search
CPC ................ G02B 13/04; G02B 21/0028; G02B 23/2407; G02B 23/243
(Continued)

(56) References Cited

U.S. PATENT DOCUMENTS

| 4,999,007 A | 3/1991 | Aoki et al. |
| 5,774,279 A | 6/1998 | Kiriki et al. |
| 6,040,949 A | 3/2000 | Ohno |

FOREIGN PATENT DOCUMENTS

| JP | 63292106 A | 11/1988 |
| JP | 64044908 A | 2/1989 |

(Continued)

OTHER PUBLICATIONS

International Search Report (ISR) and Written Opinion dated Jul. 5, 2016 issued in International Application No. PCT/JP2016/061828.

*Primary Examiner* — Scott J Sugarman
(74) *Attorney, Agent, or Firm* — Holtz, Holtz & Volek PC (57) ABSTRACT

There is provided an endoscope objective optical system with a small size and a high image quality, and in which, an adequate space for disposing a visual-field direction converting element is secured. The endoscope objective optical system, comprising in order from an object side:
a first group having a negative refractive power;
an aperture stop; and
a second group having a positive refractive power, wherein
the first group includes in order from the object side, a first lens having a negative refractive power and a visual-field direction converting member, and
the second group includes in order from the object side, a second lens having a biconvex shape and a cemented lens in which a third lens having a positive refractive power and a fourth lens having a negative refractive power are cemented in this order, and
the endoscope objective optical system satisfies the following conditional expressions (1), (2), (3), and (4)

$$2.4 \leq d_1/f \leq 4.6 \quad (1)$$

$$1.85 \leq f_2/f \leq 2.6 \quad (2)$$

$$-50 \leq r_{21}/r_{22} \leq -0.4 \quad (3)$$

$$2.01 \leq f_{03}/f \leq 2.5 \quad (4)$$

(Continued)

where, $d_1$ denotes an air conversion length from a surface on an image side of the first lens up to a surface of the aperture stop, f denotes a focal length of the overall endoscope objective optical system, $f_2$ denotes a focal length of the second group, $r_{21}$ denotes a radius of curvature of a surface on the object side of the second lens, $r_{22}$ denotes a radius of curvature of a surface on the image side of the second lens, and $f_{O3}$ denotes a focal length of the third lens.

3 Claims, 7 Drawing Sheets

(51) Int. Cl.
*A61B 1/00* (2006.01)
*G02B 9/12* (2006.01)

(58) Field of Classification Search
USPC .................................. 359/659, 660, 661, 753
See application file for complete search history.

(56) References Cited

FOREIGN PATENT DOCUMENTS

| | | |
|---|---|---|
| JP | 01191820 A | 8/1989 |
| JP | 08179226 A | 7/1996 |
| JP | 09113799 A | 5/1997 |
| JP | 09269450 A | 10/1997 |
| JP | 11237549 A | 8/1999 |

FIG. 3B
SA
FNO 6.104

ENDOSCOPE OBJECTIVE OPTICAL SYSTEM

CROSS-REFERENCE TO RELATED APPLICATION

The present application is a continuation application of PCT/JP2016/061828 filed on Apr. 12, 2016 which is based upon and claims the benefit of priority from Japanese Patent Application No. 2015-089661 filed on Apr. 24, 2015; the entire contents of which are incorporated herein by reference.

BACKGROUND OF THE INVENTION

Field of the Invention

The present invention relates to an endoscope objective optical system such as an endoscope objective optical system that is applicable to an endoscope apparatus used in fields such as a medical field and an industrial field.

Description of the Related Art

In an endoscope objective optical system, sometimes, for carrying out oblique observation, a visual-field direction converting member such as a prism is disposed in an optical system. Examples of such optical systems for oblique observation have been proposed (refer to Japanese Patent Application Laid-open Publication No. 2008-83316, Japanese Patent Application Laid-open Publication No. Hei 9-269450, Japanese Patent No. 3574484 Publication, Japanese Patent No. 4439184 Publication, Japanese Patent No. 3742484 Publication, Japanese Patent No. 558058 Publication, Japanese Patent No. 4274602 Publication, Japanese Patent Publication after Examination No. Sho 53-36787, Japanese Patent Application Laid-open Publication No. Sho 51-62053, and Japanese Patent Application Laid-open Publication No. Hei 7-294806 for example).

SUMMARY OF THE INVENTION

An endoscope objective optical system, comprises in order from an object side:

a first group having a negative refractive power;
an aperture stop; and
a second group having a positive refractive power, wherein the first group includes in order from the object side, a first lens having a negative refractive power and a visual-field direction converting member, and the second group includes in order from the object side, a second lens having a biconvex shape and a cemented lens in which a third lens having a positive refractive power and a fourth lens having a negative refractive power are cemented in this order, and the endoscope objective optical system satisfies the following conditional expressions (1), (2), (3), and (4)

$$2.4 \leq d_1/f \leq 4.6 \quad (1)$$

$$1.85 \leq f_2/f \leq 2.6 \quad (2)$$

$$-50 \leq r_{21}/r_{22} \leq -0.4 \quad (3)$$

$$2.01 \leq f_{o3}/f \leq 2.5 \quad (4)$$

where, $d_1$ denotes an air conversion length from a surface on an image side of the first lens up to a surface of the aperture stop, f denotes a focal length of the overall endoscope objective optical system, $f_2$ denotes a focal length of the second group, $r_{21}$ denotes a radius of curvature of a surface on the object side of the second lens, $r_{22}$ denotes a radius of curvature of a surface on the image side of the second lens, and $f_{o3}$ denotes a focal length of the third lens.

DESCRIPTION OF EMBODIMENTS

Reasons for and effects of adopting such arrangement for an endoscope objective optical system according to the present embodiment will be described below by using the accompanying diagrams. However, the present invention is not limited to embodiments described below.

Figure 1:
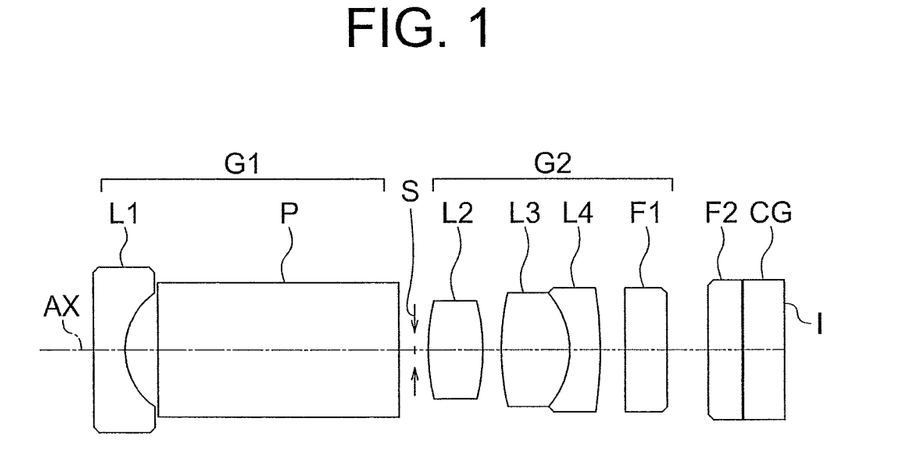
FIG. 1 is a cross-sectional view showing an arrangement of an endoscope objective optical system according to an embodiment of the present invention.

FIG. 1 is a cross-sectional view showing an arrangement of the endoscope objective optical system according to the present embodiment.

The endoscope objective optical system according to the present embodiment includes in order from an object side, a first group G1 having a negative refractive power, an aperture stop S, and a second group G2 having a positive refractive power, and the first group includes in order from the object side, a first lens L1 having a negative refractive power and a visual-field direction converting member P, and the second group G2 includes in order from the object side, a second lens L2 having a biconvex shape, and a cemented lens in which a third lens L3 having a positive refractive power and a fourth lens L4 having a negative refractive power are cemented in this order.

Moreover, the endoscope objective optical system satisfies the following conditional expressions (1), (2), and (3).

$$2.4 \leq d_1/f \leq 4.6 \tag{1}$$

$$1.85 \leq f_2/f \leq 2.6 \tag{2}$$

$$-50 \leq r_{21}/r_{22} \leq -0.4 \tag{3}$$

where, $d_1$ denotes an air conversion length from a surface on an image side of the first lens up to a surface of the aperture stop, f denotes a focal length of the overall endoscope objective optical system, $f_2$ denotes a focal length of the second group, $r_{21}$ denotes a radius of curvature of a surface on the object side of the second lens, $r_{22}$ denotes a radius of curvature of a surface on the image side of the second lens.

In such manner, in the present embodiment, for letting it to be an endoscope objective optical system having a small size and wide angle of view that can be used in an endoscope, the first lens L1 having a planoconcave shape is disposed nearest to object in the first group G1, and a negative refractive power is secured. Accordingly, it is possible to adopt an arrangement of a retro-focus type. Moreover, by disposing the visual-field direction converting member P on an image side of the first lens L1, an oblique observation is made possible. In FIG. 1, a diagram in which a visual-field direction converting member such as a prism is unfolded is shown. Therefore, the prism has been depicted as a plane parallel plate.

The positive lens L2 which contributes mainly to image formation is disposed on the object side of the second group G2. The cemented lens in which positive lens L3 and the negative lens L4 are cemented in this order is disposed at a position at which a height of a marginal ray from an optical axis becomes high on the image side of the positive lens L2. A chromatic aberration of magnification is corrected by the cemented lens. Contribution of a position where the height of the marginal ray from the optical axis is high is substantial to the correction of the chromatic aberration of magnification. Therefore, in the cemented lens, the positive lens L3 and the negative lens L4 are cemented in order from the object side so as to correct the chromatic aberration of magnification at a position where an off-axis light ray becomes higher.

Here, in an endoscope for oblique viewing, there are cases in which, a space for disposing the visual-field direction converting member has to be secured appropriately long. In this case, in a scaled down optical system in which the image pickup element is simply made small-sized, since the space for disposing the visual-field direction converting member P also becomes short, it is not preferable. In other words, it is necessary to secure a relatively long space for disposing the visual-field direction converting element with respect to a focal length of the optical system. For this reason, it is desirable to satisfy the following conditional expression (1).

$$2.4 \leq d_1/f \leq 4.6 \tag{1}$$

where, $d_1$ denotes the air conversion length from the surface on the image side of the first lens up to the surface of the aperture stop, and f denotes the focal length of the overall endoscope objective optical system Conditional expression (1) regulates the space (air conversion length) in which the visual-field direction converting member P is disposed and the focal length of the overall system.

When an upper limit value of conditional expression (1) is exceeded, the space for disposing the visual-field direction converting member P becomes large. Consequently, when an attempt is made to arrange the optical system with a diameter of the first lens maintained as it has been, a refractive power of the first lens L1 becomes large, and all aberrations are deteriorated. When a value falls below a lower limit value of conditional expression (1), the space for disposing the visual-field direction converting member P becomes small. Consequently, it becomes difficult to achieve a small-sized endoscope for oblique viewing.

It is preferable to satisfy the following conditional expression (1') instead of conditional expression (1).

$$2.6 \leq d_1/f \leq 4.4 \tag{1'}$$

Furthermore, it is more preferable to satisfy the following conditional expression (1") instead of conditional expression (1).

$$2.6 \leq d_1/f \leq 4.1 \tag{1"}$$

Moreover, when a refractive power of the second group G2 having a positive refractive power is not set appropriately, an amount of a spherical aberration and a curvature of field that occur becomes large, thereby leading to susceptibility of degradation of image quality. For this reason, it is desirable to satisfy the following conditional expression (2).

$$1.85 \leq f_2/f \leq 2.6 \tag{2}$$

where, $f_2$ denotes the focal length of the second group, and f denotes the focal length of the overall endoscope objective optical system.

When an upper limit value of conditional expression (2) is exceeded, the refractive power of the second group G2 becomes small, and correction of the curvature of field becomes excessive, and therefore it is not preferable. When a value falls below a lower limit value of conditional expression (2), the refractive power of the second group G2 becomes large, and correction of the curvature of field becomes inadequate, and therefore it is not preferable.

It is preferable to satisfy the following conditional expression (2') instead of conditional expression (2).

$$1.85 \leq f_2/f \leq 2.5 \tag{2'}$$

Furthermore, it is more preferable to satisfy the following conditional expression (2") instead of conditional expression (2).

$$1.9 \leq f_2/f \leq 2.4 \tag{2"}$$

Moreover, in order to secure a large angle of emergence and the positive refractive power for image formation, it is necessary that the second lens L2 corrects the spherical aberration and a coma aberration while maintaining the appropriate positive refractive power. For this reason, it is desirable to satisfy the following conditional expression (3).

$$-50 \leq r_{21}/r_{22} \leq -0.4 \tag{3}$$

where, $r_{21}$ denotes the radius of curvature of the surface on the object side of the second lens, $r_{22}$ denotes the radius of curvature of the surface on the image side of the second lens.

When an upper limit value of conditional expression (3) is exceeded, or when a value falls below a lower limit value of conditional expression (3), the spherical aberration and the coma aberration become substantial, and therefore it is not preferable.

It is preferable to satisfy the following conditional expression (3') instead of conditional expression (3).

$$-44 \leq r_{21}/r_{22} \leq -0.4 \tag{3'}$$

Furthermore, it is more preferable to satisfy the following conditional expression (3") instead of conditional expression (3).

$$-38 \leq r_{21}/r_{22} \leq -0.5 \tag{3"}$$

Moreover, when a refractive power of the third lens L3 is excessively large, the optical system becomes close to a telecentric optical system. Consequently, it becomes difficult to secure a large angle of emergence. As a result, a height of a light ray at a lens near an image plane I becomes high, and a diameter of the lens is susceptible to becomes large. Therefore, it is preferable arrange the optical system such that the refractive power of the third lens L3 is set to be appropriate, and the angle of emergence becomes large. For this, it is desirable to satisfy conditional expression (4).

$$1.6 \leq f_{03}/f \leq 2.5 \tag{4}$$

where, $f_{03}$ denotes a focal length of the third lens, and f denotes the focal length of the overall endoscope objective optical system.

When an upper limit value of conditional expression (4) is exceeded, the refractive power of the third lens L3 becomes small, and the angle of emergence of the light ray becomes excessively large, and it is susceptible to degradation of image quality due to shading. When a value falls below a lower limit value of conditional expression (4), the refractive power of the third lens L3 becomes large, and the angle of emergence becomes excessively small. In other words, since the diameter of the lens is susceptible to become large, it is not preferable. Furthermore, it is unfavorable for an image pickup element in which the shading characteristics are optimized, and the image quality is susceptible to be degraded.

It is preferable to satisfy the following conditional expression (4') instead of conditional expression (4).

$$1.7 \leq f_{03}/f \leq 2.4 \tag{4'}$$

Furthermore, it is more preferable to satisfy the following conditional expression (4") instead of conditional expression (4).

$$1.8 \leq f_{03}/f \leq 2.3 \tag{4"}$$

Moreover, for achieving an endoscope for oblique viewing having a small size and a superior image quality, it is necessary to set appropriately the refractive power of the first lens L1, and to maintain balance of a lens diameter and an optical performance. For this, it is desirable to satisfy the following conditional expression (5).

$$-2.2 \leq f_{01}/f \leq -1.1 \tag{5}$$

where, $f_{01}$ denotes a focal length of the first lens, and f denotes the focal length of the overall endoscope objective optical system.

When an upper limit value of conditional expression (5) is exceeded, the negative refractive power of the first lens L1 becomes large, and all aberrations are deteriorated. When a value falls below a lower limit value of conditional expression (5), the refractive power of the first lens L1 becomes small, and the diameter of the first lens L1 becomes large, and therefore it is not preferable.

It is preferable to satisfy the following conditional expression (5') instead of conditional expression (5).

$$-2.0 \leq f_{01}/f \leq -1.1 \tag{5'}$$

Furthermore, it is more preferable to satisfy the following conditional expression (5") instead of conditional expression (5).

$$-1.8 \leq f_{01}/f \leq -1.1 \tag{5"}$$

Moreover, it is desirable that the optical system is compact in a longitudinal direction of the endoscope while securing the space for disposing the long visual-field direction converting member P. For this, it is desirable to satisfy the following conditional expression (6).

$$0.5 \leq d_1/d_2 \leq 1.2 \tag{6}$$

where, $d_1$ denotes the air conversion length from the surface on the image side of the first lens up to the surface of the aperture stop, and $d_2$ denotes an air conversion length from the surface of the aperture stop up to an image plane.

When an upper limit value of conditional expression (6) is exceeded, the space for disposing the visual-field direction converting member P becomes excessively large, and the diameter of the first lens L1 becomes large. When a value fails below a lower limit value of conditional expression (6), the optical system becomes excessively large in the longitudinal direction of the endoscope, and therefore it is not preferable.

It is preferable to satisfy the following conditional expression (6') instead of conditional expression (6).

$$0.55 \leq d_1/d_2 \leq 1.15 \tag{6'}$$

Furthermore, it is more preferable to satisfy the following conditional expression (6") instead of conditional expression (6).

$$0.6 \leq d_1/d_2 \leq 1.1 \tag{6"}$$

Moreover, it is desirable that the present embodiment satisfies the following conditional expression (7).

$$1.8 \leq f_{02}/f \leq 3.2 \tag{7}$$

where, $f_{02}$ denotes a focal length of the second lens L2, and f denotes the focal length of the overall endoscope objective optical system.

When an upper limit value of conditional expression (7) is exceeded, the refractive power of the second lens L2 becomes excessively small. Consequently, the curvature of field is corrected excessively, and it is not preferable. When a value falls below a lower limit value of conditional expression (7), the refractive power of the second lens L2 becomes large. Consequently, correction of the spherical aberration becomes inadequate, and therefore it is not preferable.

It is preferable to satisfy the following conditional expression (7') instead of conditional expression (7).

$$1.9 \leq f_{02}/f \leq 3.1 \quad (7')$$

Furthermore, it is more preferable to satisfy the following conditional expression (7") instead of conditional expression (7).

$$2 \leq f_{02}/f \leq 3 \quad (7'')$$

Moreover, for achieving an endoscope image of a superior quality, it is desirable to correct the inadequately corrected spherical aberration and the curvature of field occurring in the second lens L2 having a positive refractive power and the third lens L3 having a positive refractive power, by a fourth lens L4 having an appropriate negative refractive power. For this, it is desirable to satisfy the following conditional expression (8).

$$-2.8 \leq f_{04}/f \leq -1.2 \quad (8)$$

where, $f_{04}$ denotes a focal length of the fourth lens L4, and f denotes the focal length of the overall endoscope objective optical system.

When an upper limit value of conditional expression (8) is exceeded, the refractive power of the fourth lens L4 becomes large. Consequently, the curvature of field is corrected excessively, and therefore it is not preferable. When a value falls below a lower limit value of conditional expression (8), the refractive power of the fourth lens L4 becomes small. Consequently, correction of the spherical aberration is inadequate, and therefore it is not preferable.

It is preferable to satisfy the following conditional expression (8') instead of conditional expression (8).

$$-2.7 \leq f_{04}/f \leq -1.5 \quad (8')$$

Furthermore, it is more preferable to satisfy the following conditional expression (8") instead of conditional expression (8).

$$-2.6 \leq f_{04}/f \leq -1.8 \quad (8'')$$

Moreover, for small-sizing, it is desirable to make a diameter of the first group G1 small. For this, it is desirable to satisfy the following conditional expression (9).

$$0.6 \leq en/f \leq 1.15 \quad (9)$$

where, en denotes a position of a light ray with the maximum image height at an entrance pupil, and f denotes the focal length of the overall endoscope objective optical system.

When an upper limit value of conditional expression (9) is exceeded, since the diameter of the first lens L1 having a negative refractive power becomes large, it is not preferable. When a value falls below a lower limit value of conditional expression (9), the refractive power of the first lens L1 having a negative refractive power becomes large, and therefore it is not preferable.

It is preferable to satisfy the following conditional expression (9') instead of conditional expression (9).

$$0.64 \leq en/f \leq 1.1 \quad (9')$$

Furthermore, it is more preferable to satisfy the following conditional expression (9") instead of conditional expression (9).

$$0.68 \leq en/f \leq 1.05 \quad (9'')$$

Moreover, it is desirable that the present embodiment satisfies the following conditional expression (10).

$$-6.5 \leq ex/f \leq -2.8 \quad (10)$$

where, ex denotes a position of a light ray having the maximum image height at an exit pupil, and f denotes the focal length of the overall endoscope objective optical system.

When an upper limit value of conditional expression (10) is exceeded, an angle of emergence of a light ray becomes large. In other words, the refractive power of the second lens L2 becomes large, and the spherical aberration is deteriorated. When a value falls below a lower limit value of conditional expression (10), the angle of emergence of a light ray becomes small. Consequently, it is unfavorable for an image pickup element in which the shading characteristics are optimized.

It is preferable to satisfy the following conditional expression (10') instead of conditional expression (10).

$$-5.8 \leq ex/f \leq -3.3 \quad (10')$$

Furthermore, it is more preferable to satisfy the following conditional expression (10") instead of conditional expression (10).

$$-5.1 \leq ex/f \leq -3.8 \quad (10'')$$

EXAMPLE 1

Figure 2A:
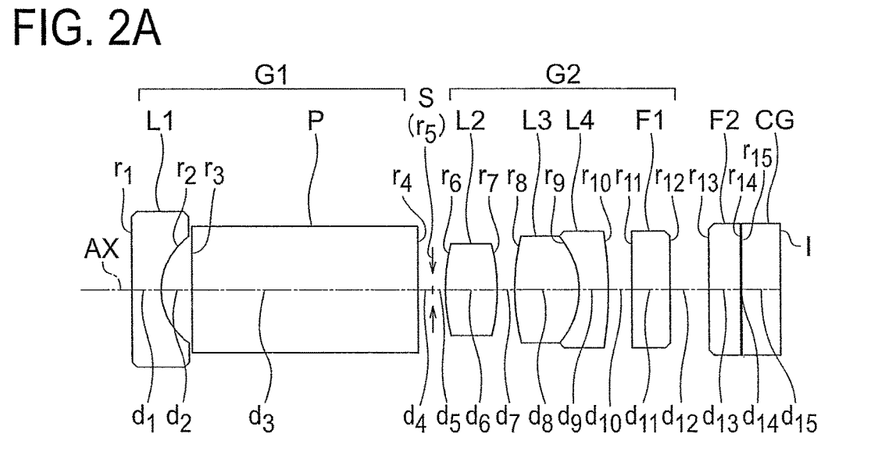
FIG. 2A is a cross-sectional view showing an arrangement of an endoscope objective optical system according to an example 1 of the present invention.
Figure 2B:
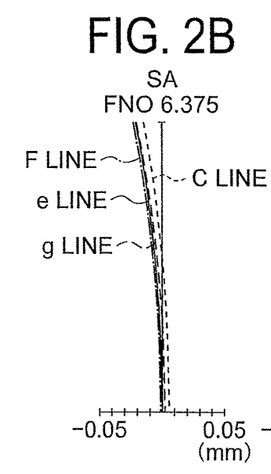
FIG. 2B, FIG. 2C, FIG. 2D, and FIG. 2E are aberration diagrams showing a spherical aberration (SA), an astigmatism (AS), a distortion (DT), and a chromatic aberration of magnification (CC) respectively of the example 1.
Figure 2C:
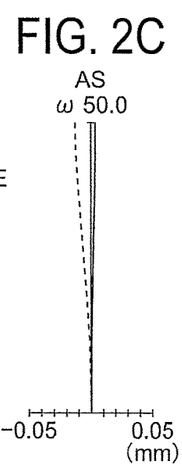
Figure 2D:
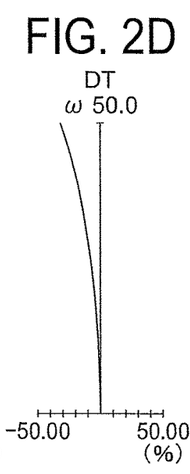
Figure 2E:
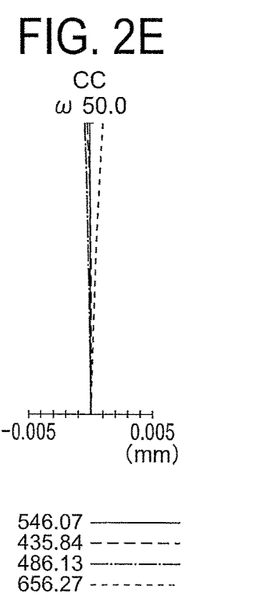

An endoscope objective optical system according to an example 1 will be described below. FIG. 2A is a cross-sectional view of the endoscope objective optical system according to the present example. In all examples that follow, a visual-field direction converting member P such as a prism is shown to be in an unfolded state. Therefore, the visual-field direction converting member P is illustrated as a plane parallel plate having an optical path length equivalent to that of prism.

In the present example, the endoscope objective optical system includes in order from an object side, a first group G1 having a negative refractive power, an aperture stop S, and a second group G2 having a positive refractive power.

The first group G1 includes in order from the object side, a planoconcave negative lens L1 and a visual-field direction converting member P. The second group G2 includes a biconvex positive lens L2, a biconvex positive lens L3, a negative meniscus lens L4 having a convex surface directed toward an image side, and a plane parallel plate F1. Here, the positive lens L3 and the negative meniscus lens L4 are cemented. A plane parallel plate F2 and a cover glass CG are disposed on the image side of the second group G2.

The plane parallel plate F1 is a filter with a coating applied thereto for cutting specific wavelengths such as 1060 nm of YAG (yttrium aluminum garnet) laser and 810 nm of semiconductor laser, or an infra-red region.

FIG. 2B, FIG. 2C, FIG. 2D, and FIG. 2E show a spherical aberration (SA), an astigmatism (AS), a distortion (DT), and a chromatic aberration of magnification (CC) respectively of the present example. These aberration diagrams are shown for wavelengths of 546.07 nm (e-line), 435.84 nm (g-line), 486.13 nm (F-line), and 656.27 nm (C-line). Moreover, in each diagram, Fno denotes an F-number and ω denotes a half angle of view. It is similar for the aberration diagrams. Furthermore, the image height is 0.5 mm, Fno is 6.375, and the half angle of view is 50.0°.

EXAMPLE 2

Figure 3A:
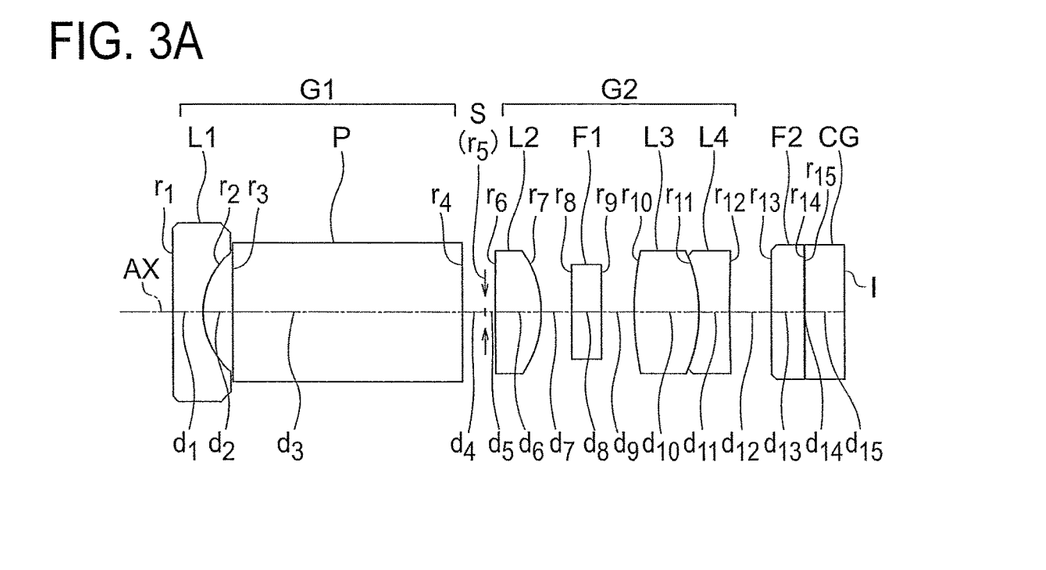
FIG. 3A is a cross-sectional view showing an arrangement of an endoscope objective optical system according to an example 2 of the present invention.
Figure 3B:
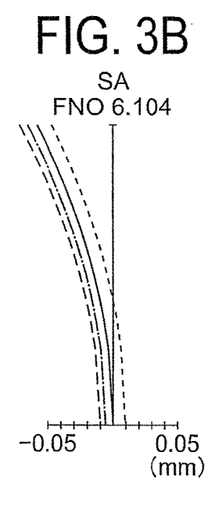
FIG. 3B, FIG. 3C, FIG. 3D, and FIG. 3E are aberration diagrams showing a spherical aberration (SA), an astigmatism (AS), a distortion (DT), and a chromatic aberration of magnification (CC) respectively of the example 2.
Figure 3C:
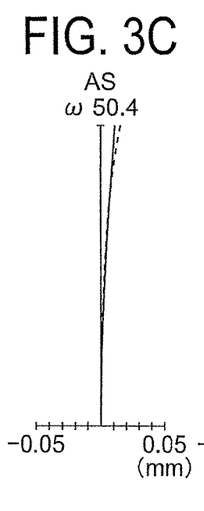
Figure 3D:
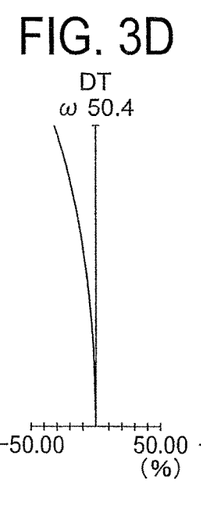
Figure 3E:
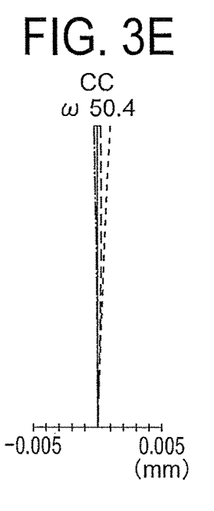

FIG. 3A is a cross-sectional view of an endoscope objective optical system according to an example 2. In the present example, the endoscope objective optical system includes in order from an object side, a first group G1 having a negative refractive power, an aperture stop S, and a second group G2 having a positive refractive power.

The first group G1 includes in order from an object side, a planoconcave negative lens L1 and a visual-field direction converting member P. The second group G2 includes a biconvex positive lens L2, a plane parallel plate F1, a biconvex positive lens L3, and a negative meniscus lens L4 having a convex surface directed toward an image side. Here, the positive lens L3 and the negative meniscus lens L4 are cemented. A plane parallel plate F2 and a cover glass CG are disposed on the image side of the second group G2.

The plane parallel plate F1 is a filter with a coating applied thereto for cutting specific wavelengths such as 1060 nm YAG laser and 810 nm of semiconductor laser, or an infra-red region.

FIG. 3B, FIG. 3C, FIG. 3D, and FIG. 3E show a spherical aberration (SA), an astigmatism (AS), a distortion (DT), and a chromatic aberration of magnification (CC) respectively of the present example. The image height is 0.5 mm, Fno is 6.104, and the half angle of view is 50.4°.

EXAMPLE 3

Figure 4A:
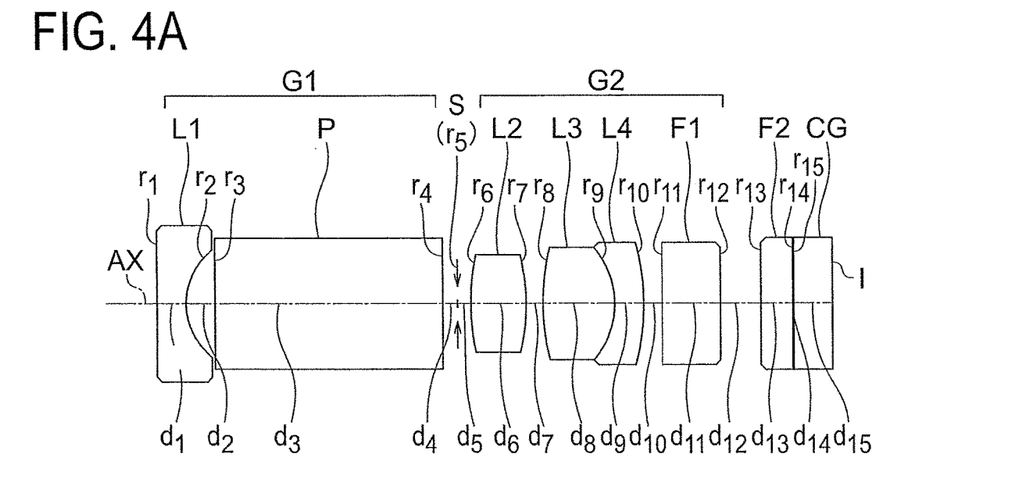
FIG. 4A is a cross-sectional view showing an arrangement of an endoscope objective optical system according to an example 3 of the present invention.
Figure 4B:
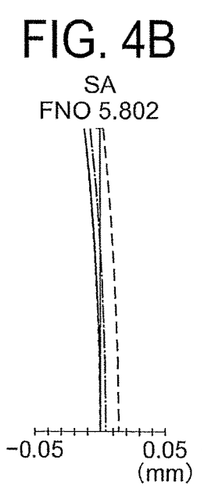
FIG. 4B, FIG. 4C, FIG. 4D, and FIG. 4E are aberration diagrams showing a spherical aberration (SA), an astigmatism (AS), a distortion (DT), and a chromatic aberration of magnification (CC) respectively of the example 3.
Figure 4C:
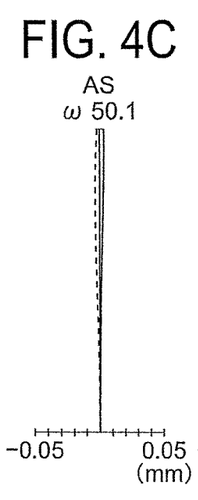
Figure 4D:
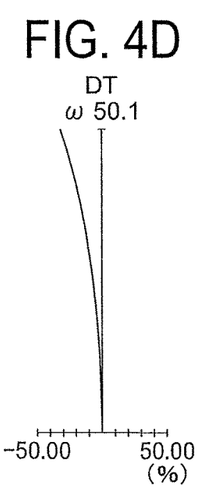
Figure 4E:
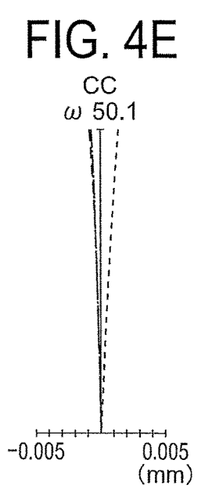

FIG. 4A is a cross-sectional view of an endoscope objective optical system according to an example 3. In the present example, the endoscope objective optical system includes in order from an object side, a first group G1 having a negative refractive power, an aperture stop S, and a second group G2 having a positive refractive power.

The first group G1 includes in order from an object side, a planoconcave negative lens L1 and a visual-field direction converting member P. The second group G2 includes a biconvex positive lens L2, a biconvex positive lens L3, a negative meniscus lens L4 having a convex surface directed toward an image side, and a plane parallel plate F1. Here, the positive lens L3 and the negative meniscus lens L4 are cemented. A plane parallel plate F2 and a cover glass CG are disposed on the image side of the second group G2.

The plane parallel plate F1 is a filter with a coating applied thereto for cutting specific wavelengths such as 1060 nm of YAG laser and 810 nm of semiconductor laser, or an infra-red region.

FIG. 4B, FIG. 4C, FIG. 4D, and FIG. 4E show a spherical aberration (SA), an astigmatism (AS), a distortion (DT), and a chromatic aberration of magnification (CC) respectively of the present example. The image height is 0.5 mm, Fno is 5.802, and the half angle of view is 50.1°.

EXAMPLE 4

Figure 5A:
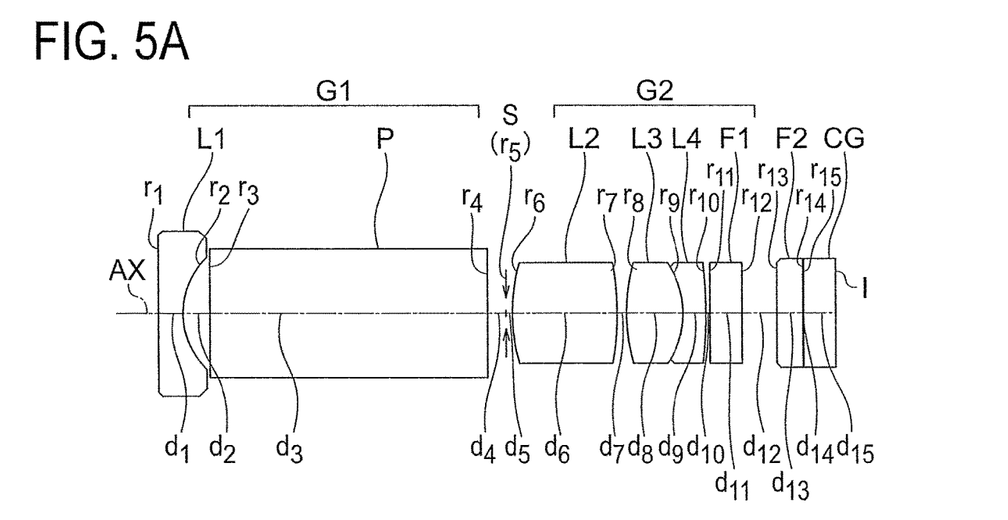
FIG. 5A is a cross-sectional view showing an arrangement of an endoscope objective optical system according to an example 4 of the present invention.
Figure 5B:
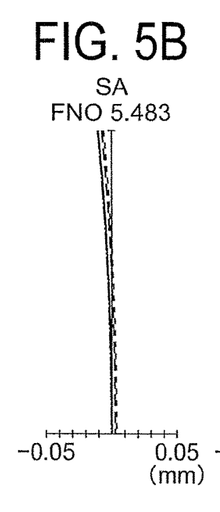
FIG. 5B, FIG. 5C, FIG. 5D, and FIG. 5E are aberration diagrams showing a spherical aberration (SA), an astigmatism (AS), a distortion (DT), and a chromatic aberration of magnification (CC) respectively of the example 4.
Figure 5C:
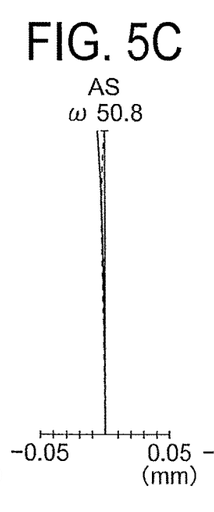
Figure 5D:
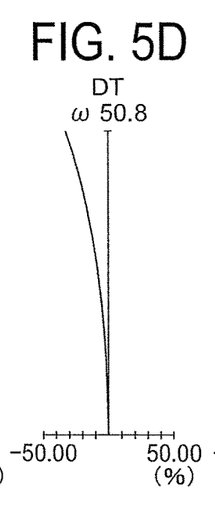
Figure 5E:
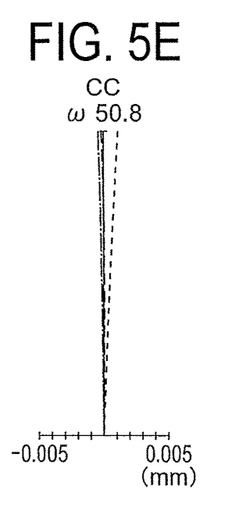

FIG. 5A is a cross-sectional view of an endoscope objective optical system according to an example 4. In the present example, the endoscope objective optical system includes in order from an object side, a first group G1 having a negative refractive power, an aperture stop S, and a second group G2 having a positive refractive power.

The first group G1 includes in order from the object side, a planoconcave negative lens L1 and a visual-field direction converting member P. The second group G2 includes in order from the object side, a biconvex positive lens L2, a biconvex positive lens L3, a negative meniscus lens L4 having a convex surface directed toward an image side, and a plane parallel plate F1. Here, the biconvex positive lens L3 and the negative meniscus lens L4 are cemented. A plane parallel plate F2 and a cover glass CG are disposed on the image side of the second group G2.

The plane parallel plate F1 is a filter with a coating applied thereto for cutting specific wavelengths such as 1060 nm of YAG laser, and 810 nm of semiconductor laser, or an infra-red region.

FIG. 5B, FIG. 5C, FIG. 5D, and FIG. 5E show a spherical aberration (SA), an astigmatism (AS), a distortion (DT), and a chromatic aberration of magnification (CC) respectively of the present example. The image height is 0.5 mm, Fno is 5.483, and the half angle of view is 50.8°.

EXAMPLE 5

Figure 6A:
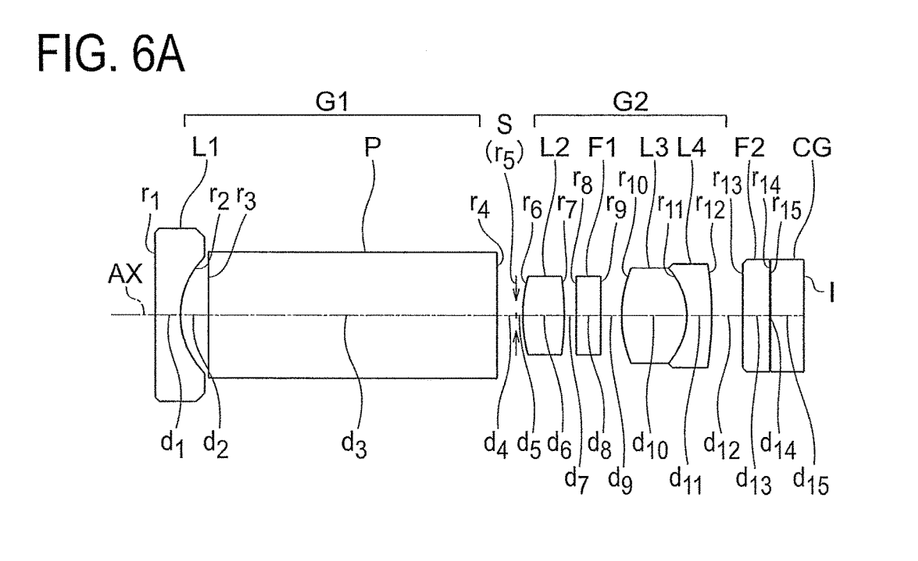
FIG. 6A is a cross-sectional view showing an arrangement of an endoscope objective optical system according to an example 5 of the present invention.
Figure 6B:
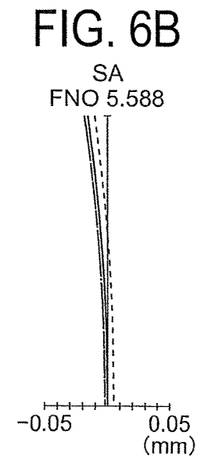
FIG. 6B, FIG. 6C, FIG. 6D, and FIG. 6E are aberration diagrams showing a spherical aberration (SA), an astigmatism (AS), a distortion (DT), and a chromatic aberration of magnification (CC) respectively of the example 5.
Figure 6C:
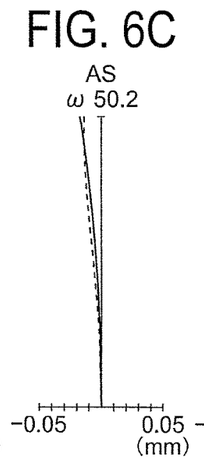
Figure 6D:
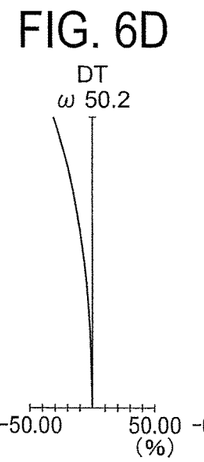
Figure 6E:
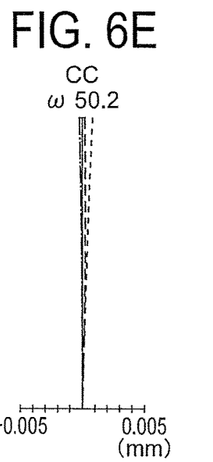

FIG. 6A is a cross-sectional view of an endoscope objective optical system according to an example 5. In the present example, the endoscope objective optical system includes in order from an object side, a first group G1 having a negative refractive power, an aperture stop S, and a second group G2 having a positive refractive power.

The first group G1 includes in order from the object side, a planoconcave negative lens L1 and a visual-field direction converting member P. The second group G2 includes a biconvex positive lens L2, a plane parallel plate F1, a biconvex positive lens L3, and a negative meniscus lens L4 having a convex surface directed toward an image side. A plane parallel plate F2 and a cover glass CG are disposed on the image side of the second group G2.

The plane parallel plate F1 is a filter with a coating applied thereto for cutting specific wavelengths such as 1060 nm of YAG laser, and 810 nm of semiconductor laser, or an infra-red region.

FIG. 6B, FIG. 6C, FIG. 6D, and FIG. 6E show a spherical aberration (SA), an astigmatism (AS), a distortion (DT), and a chromatic aberration of magnification (CC) respectively of the present example. The image height is 0.5 mm, Fno is 5.588, and the half angle of view is 50.2°.

EXAMPLE 6

Figure 7A:
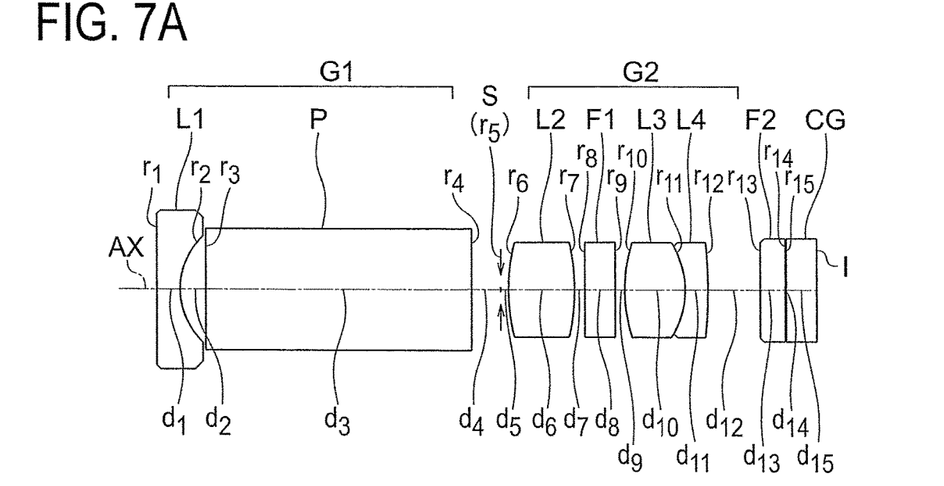
FIG. 7A is a cross-sectional view showing an arrangement of an endoscope objective optical system according to an example 6 of the present invention.
Figure 7B:
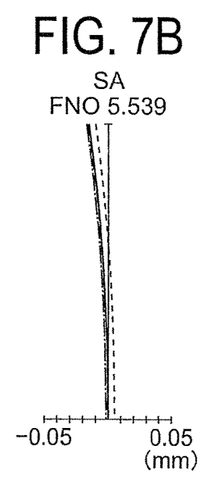
FIG. 7B, FIG. 7C, FIG. 7D, and FIG. 7E are aberration diagrams showing a spherical aberration (SA), an astigmatism (AS), a distortion (DT), and a chromatic aberration of magnification (CC) respectively of the example 6.
Figure 7C:
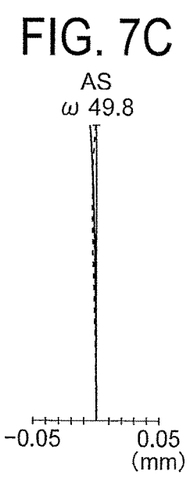
Figure 7D:
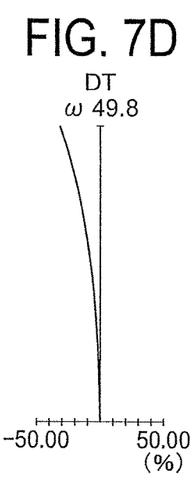
Figure 7E:
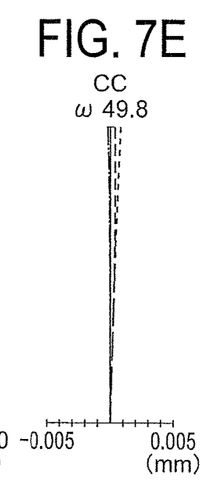

FIG. 7A is a cross-sectional view of an endoscope objective optical system according to an example 6. In the present example, the endoscope objective optical system includes in order from an object side, a first group G1 having a negative refractive power, an aperture stop S, and a second group G2 having a positive refractive power.

The first group G1 includes in order from the object side, a planoconcave negative lens L1 and a visual-field direction converting member P. The second group G2 includes a biconvex positive lens L2, a plane parallel plate F1, a biconvex positive lens L3, and a negative meniscus lens L4 having a convex surface directed toward an image side. Here, the positive lens L3 and the negative meniscus lens L4 are cemented. A plane parallel plate F2 and a cover glass CG are disposed on the image side of second group G2.

The plane parallel plate F1 is a filter with a coating applied thereto for cutting specific wavelengths such as 1060 nm of YAG laser, and 810 nm of semiconductor laser, or an infra-red region.

FIG. 7B, FIG. 7C, FIG. 7D, and FIG. 7E show a spherical aberration (SA), an astigmatism (AS), a distortion (DT), and a chromatic aberration of magnification (CC) respectively of the present example. The image height is 0.5 mm, Fno is 5.539, and the half angle of view is 49.8°.

Numerical data for each example is shown below. Regarding symbols, r denotes a radius of curvature of each lens surface, d denotes a distance between two lens surfaces, nd denotes a refractive index of each lens for an e-line, νd denotes Abbe's number for each lens, and Fn denotes an F-number.

EXAMPLE 1

Unit mm
Surface data

| Surface no. | r | d | nd | νd |
|---|---|---|---|---|
| Object plane | ∞ | 4.3605 | | |
| 1 | ∞ | 0.2907 | 1.88815 | 40.76 |
| 2 | 0.6463 | 0.3101 | | |
| 3 | ∞ | 2.2674 | 1.88815 | 40.76 |
| 4 | ∞ | 0.1453 | | |
| 5(Stop) | ∞ | 0.126 | | |
| 6 | 1.9264 | 0.5136 | 1.81078 | 40.92 |
| 7 | −1.9264 | 0.1744 | | |
| 8 | 2.2926 | 0.6395 | 1.51977 | 52.43 |
| 9 | −0.814 | 0.2907 | 1.93429 | 18.90 |
| 10 | −3.7607 | 0.2326 | | |
| 11 | ∞ | 0.3876 | 1.523 | 65.13 |
| 12 | ∞ | 0.3886 | | |
| 13 | ∞ | 0.3198 | 1.51825 | 64.14 |
| 14 | ∞ | 0.0097 | 1.515 | 64.00 |
| 15 | ∞ | 0.3876 | 1.507 | 63.26 |
| Image plane | ∞ | | | |

Various data
focal length  0.6187
Fno.  6.375

EXAMPLE 2

Unit mm
Surface data

| Surface no. | r | d | nd | νd |
|---|---|---|---|---|
| Object plane | ∞ | 5.4264 | | |
| 1 | ∞ | 0.2955 | 1.88815 | 40.76 |
| 2 | 0.7592 | 0.2907 | | |
| 3 | ∞ | 2.2481 | 1.88815 | 40.76 |
| 4 | ∞ | 0.2229 | | |
| 5(Stop) | ∞ | 0.0969 | | |
| 6 | 39.5292 | 0.4464 | 1.77621 | 49.60 |
| 7 | −1.0693 | 0.2958 | | |
| 8 | ∞ | 0.2907 | 1.523 | 65.13 |
| 9 | ∞ | 0.3147 | | |
| 10 | 2.7791 | 0.6343 | 1.73234 | 54.68 |
| 11 | −1.4607 | 0.3018 | 1.97189 | 17.47 |
| 12 | 18.6587 | 0.4059 | | |
| 13 | ∞ | 0.3198 | 1.51825 | 64.14 |
| 14 | ∞ | 0.0097 | 1.515 | 64.00 |
| 15 | ∞ | 0.3876 | 1.507 | 63.26 |
| Image plane | ∞ | | | |

Various data
focal length  0.6148
Fno.  6.104

EXAMPLE 3

Unit mm
Surface data

| Surface no. | r | d | nd | νd |
|---|---|---|---|---|
| Object plane | ∞ | 5.1357 | | |
| 1 | ∞ | 0.2907 | 1.88815 | 40.76 |
| 2 | 0.6741 | 0.2904 | | |
| 3 | ∞ | 2.2774 | 1.88815 | 40.76 |
| 4 | ∞ | 0.1453 | | |
| 5(Stop) | ∞ | 0.1316 | | |
| 6 | 2.3270 | 0.5463 | 1.79012 | 44.20 |
| 7 | −2.0048 | 0.1708 | | |
| 8 | 2.3145 | 0.7102 | 1.51825 | 64.14 |
| 9 | −0.8563 | 0.2907 | 1.93429 | 18.90 |
| 10 | −2.3840 | 0.1870 | | |
| 11 | ∞ | 0.5814 | 1.523 | 65.13 |
| 12 | ∞ | 0.4016 | | |
| 13 | ∞ | 0.3198 | 1.51825 | 64.14 |
| 14 | ∞ | 0.0097 | 1.515 | 64.00 |
| 15 | ∞ | 0.3876 | 1.507 | 63.26 |
| Image plane | ∞ | | | |

Various data
focal length  0.6225
Fno.  5.802

EXAMPLE 4

Unit mm
Surface data

| Surface no. | r | d | nd | νd |
|---|---|---|---|---|
| Object plane | ∞ | 6.1047 | | |
| 1 | ∞ | 0.2955 | 1.88815 | 40.76 |
| 2 | 0.9467 | 0.3246 | | |
| 3 | ∞ | 3.3794 | 1.88815 | 40.76 |
| 4 | ∞ | 0.2229 | | |
| 5(Stop) | ∞ | 0.0775 | | |
| 6 | 2.1943 | 1.2617 | 1.88815 | 40.76 |
| 7 | −3.316 | 0.1163 | | |
| 8 | 2.2462 | 0.6810 | 1.59143 | 61.14 |
| 9 | −1.0563 | 0.2821 | 1.93429 | 18.90 |
| 10 | −5.2068 | 0.0484 | | |
| 11 | ∞ | 0.3876 | 1.523 | 65.13 |
| 12 | ∞ | 0.4244 | | |
| 13 | ∞ | 0.3198 | 1.51825 | 64.14 |
| 14 | ∞ | 0.0097 | 1.515 | 64.00 |
| 15 | ∞ | 0.3876 | 1.507 | 63.26 |
| Image plane | ∞ | | | |

Various data
focal length  0.6189
Fno.  5.483

EXAMPLE 5

Unit mm
Surface data

| Surface no. | r | d | nd | νd |
|---|---|---|---|---|
| Object plane | ∞ | 5.4264 | | |
| 1 | ∞ | 0.2955 | 1.88815 | 40.76 |
| 2 | 0.9620 | 0.3246 | | |
| 3 | ∞ | 3.3794 | 1.88815 | 40.76 |
| 4 | ∞ | 0.2229 | | |
| 5(Stop) | ∞ | 0.0775 | | |
| 6 | 1.7223 | 0.4823 | 1.73234 | 54.68 |
| 7 | −3.3188 | 0.1367 | | |
| 8 | ∞ | 0.2907 | 1.523 | 65.13 |
| 9 | ∞ | 0.2422 | | |
| 10 | 1.4769 | 0.7630 | 1.5343 | 48.84 |
| 11 | −0.8247 | 0.2907 | 1.93429 | 18.90 |
| 12 | −3.8931 | 0.3604 | | |

-continued

Unit mm
Surface data

| Surface no. | r | d | nd | vd |
|---|---|---|---|---|
| 13 | ∞ | 0.3198 | 1.51825 | 64.14 |
| 14 | ∞ | 0.0097 | 1.515 | 64.00 |
| 15 | ∞ | 0.3876 | 1.507 | 63.26 |
| Image plane | ∞ | | | |
| Various data | | | | |
| focal length | 0.6170 | | | |
| Fno. | 5.588 | | | |

EXAMPLE 6

Unit mm
Surface data

| Surface no. | r | d | nd | vd |
|---|---|---|---|---|
| Object plane | ∞ | 5.4264 | | |
| 1 | ∞ | 0.2955 | 1.88815 | 40.76 |
| 2 | 0.9467 | 0.3246 | | |
| 3 | ∞ | 3.3794 | 1.88815 | 40.76 |
| 4 | ∞ | 0.3682 | | |
| 5(Stop) | ∞ | 0.0969 | | |
| 6 | 2.5285 | 0.8326 | 1.79196 | 47.37 |
| 7 | −2.8131 | 0.1268 | | |
| 8 | ∞ | 0.3876 | 1.523 | 65.13 |
| 9 | ∞ | 0.1223 | | |
| 10 | 2.0400 | 0.7674 | 1.59143 | 61.14 |
| 11 | −1.1548 | 0.2907 | 1.93429 | 18.90 |
| 12 | −6.1764 | 0.6617 | | |
| 13 | ∞ | 0.3198 | 1.51825 | 64.14 |
| 14 | ∞ | 0.0097 | 1.515 | 64.00 |
| 15 | ∞ | 0.3876 | 1.507 | 63.26 |
| Image plane | ∞ | | | |
| Various data | | | | |
| focal length | 0.6300 | | | |
| Fno. | 5.539 | | | |

Values of each of the conditional expressions are shown below;

| Conditional Expression | Example 1 | Example 2 | Example 3 |
|---|---|---|---|
| (1) $d_1/f$ | 2.68 | 2.77 | 2.64 |
| (2) $f_2/f$ | 1.92 | 1.95 | 2.03 |
| (3) $r_{21}/r_{22}$ | −1.00 | −36.97 | −1.16 |
| (4) $f_{03}/f$ | 2.01 | 2.27 | 2.10 |
| (5) $f_{01}/f$ | −1.18 | −1.39 | −1.22 |
| (6) $d_1/d_2$ | 0.66 | 0.67 | 0.61 |
| (7) $f_{02}/f$ | 2.04 | 2.19 | 2.32 |
| (8) $f_{04}/f$ | −1.89 | −2.25 | −2.53 |
| (9) en/f | 0.75 | 0.82 | 0.76 |
| (10) ex/f | −4.06 | −4.13 | −4.78 |

| Conditional Expression | Example 4 | Example 5 | Example 6 |
|---|---|---|---|
| (1) $d_1/f$ | 3.78 | 3.79 | 3.94 |
| (2) $f_2/f$ | 2.28 | 2.15 | 2.36 |
| (3) $r_{21}/r_{22}$ | −0.66 | −0.52 | −0.90 |
| (4) $f_{03}/f$ | 2.13 | 1.81 | 2.17 |
| (5) $f_{01}/f$ | −1.72 | −1.76 | −1.69 |
| (6) $d_1/d_2$ | 0.89 | 0.97 | 0.88 |
| (7) $f_{02}/f$ | 2.69 | 2.62 | 2.87 |
| (8) $f_{04}/f$ | −2.37 | −1.90 | −2.48 |
| (9) en/f | 0.99 | 1.02 | 1.01 |
| (10) ex/f | −4.76 | −4.00 | −4.95 |

As described above, the present invention is useful for an endoscope objective optical system and particularly to an endoscope objective optical system for oblique viewing.

According to the present invention, an effect is shown that it is possible to achieve an endoscope objective optical system with a small size and a superior image quality, and in which, an adequate space for disposing a visual-field direction converting element is provided.

What is claimed is:

1. An endoscope objective optical system, comprising in order from an object side:
   a first group having a negative refractive power;
   an aperture stop; and
   a second group having a positive refractive power, wherein
   the first group includes in order from the object side, a first lens having a negative refractive power and a visual-field direction converting member, and
   the second group includes in order from the object side, a second lens having a biconvex shape and a cemented lens in which a third lens having a positive refractive power and a fourth lens having a negative refractive power are cemented in this order, and
   the endoscope objective optical system satisfies the following conditional expressions (1), (2), (3), and (4)

$$2.4 \leq d_1/f \leq 4.6 \quad (1)$$

$$1.85 \leq f_2/f \leq 2.6 \quad (2)$$

$$-50 \leq r_{21}/r_{22} \leq -0.4 \quad (3)$$

$$2.01 \leq f_{03}/f \leq 2.5 \quad (4)$$

where,
$d_1$ denotes an air conversion length from a surface on an image side of the first lens up to a surface of the aperture stop,
f denotes a focal length of the overall endoscope objective optical system,
$f_2$ denotes a focal length of the second group,
$r_{21}$ denotes a radius of curvature of a surface on the object side of the second lens,
$r_{22}$ denotes a radius of curvature of a surface on the image side of the second lens, and
$f_{03}$ denotes a focal length of the third lens.

2. The endoscope objective optical system according to claim 1, wherein the endoscope objective optical system satisfies the following conditional expression (5)

$$-2.2 \leq f_{01}/f \leq -1.1 \quad (5)$$

where,
$f_{01}$ denotes a focal length of the first lens, and
f denotes the focal length of the overall endoscope objective optical system.

3. The endoscope objective optical system according to claim 1, wherein the endoscope objective optical system satisfies the following conditional expression (6)

$$0.5 \leq d_1/d_2 \leq 1.2 \quad (6)$$

where,
$d_1$ denotes the air conversion length from the surface on the image side of the first lens up to the surface of the aperture stop, and
$d_2$ denotes an air conversion length from the surface of the aperture stop up to an image plane.

* * * * *